US010265059B2

(12) United States Patent
Rowe et al.

(10) Patent No.: US 10,265,059 B2
(45) Date of Patent: Apr. 23, 2019

(54) TRANS-SEPTAL CLOSURE AND PORT DEVICE

(71) Applicant: Edwards Lifesciences Corporation, Irvine, CA (US)

(72) Inventors: Stanton J. Rowe, Newport Coast, CA (US); Ming H. Wu, Tustin, CA (US); Jinny Lee, Corona del Mar, CA (US); Ralph Schneider, Trabuco Canyon, CA (US); Sergio Delgado, Irvine, CA (US); Ilan Tamir, Hefzi-Bah (IL)

(73) Assignee: Edwards Lifesciences Corporation, Irvine, CA (US)

( * ) Notice: Subject to any disclaimer, the term of this patent is extended or adjusted under 35 U.S.C. 154(b) by 79 days.

(21) Appl. No.: 15/416,595

(22) Filed: Jan. 26, 2017

(65) Prior Publication Data
US 2017/0224323 A1 Aug. 10, 2017

Related U.S. Application Data

(60) Provisional application No. 62/291,258, filed on Feb. 4, 2016.

(51) Int. Cl.
*A61B 17/02* (2006.01)
*A61B 17/00* (2006.01)
*A61F 2/24* (2006.01)

(52) U.S. Cl.
CPC ...... *A61B 17/0218* (2013.01); *A61B 17/0057* (2013.01); *A61F 2/2427* (2013.01);
(Continued)

(58) Field of Classification Search
CPC ..... A61B 17/04; A61B 17/02; A61B 17/0218; A61B 17/0057; A61B 2017/00592;
(Continued)

(56) References Cited

U.S. PATENT DOCUMENTS 6,346,074 B1 * 2/2002 Roth ................ A61B 17/00234
600/121
7,967,840 B2 6/2011 Chanduszko
(Continued)

OTHER PUBLICATIONS

Int'l. Search Report for PCT/US2017/015662, dated May 11, 2017.

*Primary Examiner* — Victor Nguyen
(74) *Attorney, Agent, or Firm* — Jie Lian; Klarquist Sparkman, LLP

(57) ABSTRACT

A septal closure and port device for implantation in the atrial septum of a patient's heart includes an expandable frame having a central portion defining a lumen, and first and second opposing end portions. The frame is configured to expand and contract between a compressed, tubular configuration for delivery through the patient's vasculature and an expanded configuration in which the first and second end portions extend radially outwardly from the opposite ends of the central portion. The device can further include a valve member supported on the frame and positioned to block at least the flow of blood from the left atrium to the right atrium through the lumen of the frame. The valve member is configured to permit a medical instrument to be inserted through the lumen and into the left atrium, such as for performing a subsequent medical procedure in the left side of the heart.

20 Claims, 10 Drawing Sheets

(52) U.S. Cl.
CPC ......... *A61B 2017/00575* (2013.01); *A61B 2017/00592* (2013.01); *A61B 2017/00597* (2013.01); *A61B 2017/00601* (2013.01); *A61B 2017/00606* (2013.01); *A61B 2017/00623* (2013.01); *A61B 2017/00632* (2013.01); *A61B 2017/0225* (2013.01); *A61B 2017/0237* (2013.01)

(58) Field of Classification Search
CPC ......... A61B 2017/00601; A61B 2017/00632; A61B 2017/00637; A61B 2017/00654
See application file for complete search history.

(56) References Cited

U.S. PATENT DOCUMENTS

| | | |
|---|---|---|
| 8,419,767 B2 | 4/2013 | Al-Qbandi et al. |
| 8,480,706 B2 | 7/2013 | Chanduszko et al. |
| 8,480,709 B2 | 7/2013 | Chanduszko |
| 2002/0111585 A1 | 8/2002 | Lafontaine |
| 2003/0139819 A1 | 7/2003 | Rogers et al. |
| 2014/0074155 A1 | 3/2014 | Rothstein et al. |
| 2015/0142049 A1 | 5/2015 | Delgado et al. |
| 2015/0313599 A1 | 11/2015 | Johnson et al. |

* cited by examiner

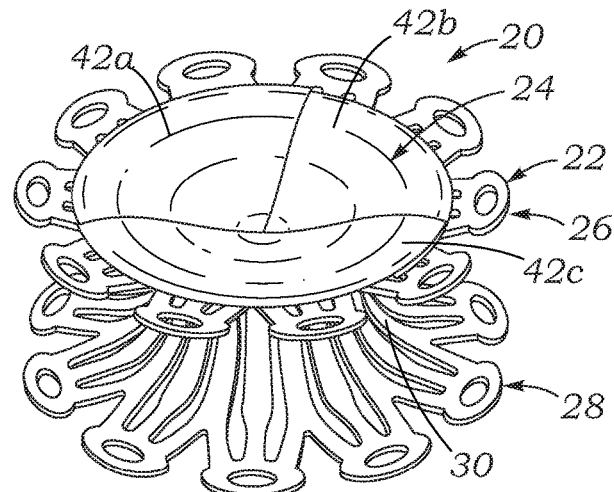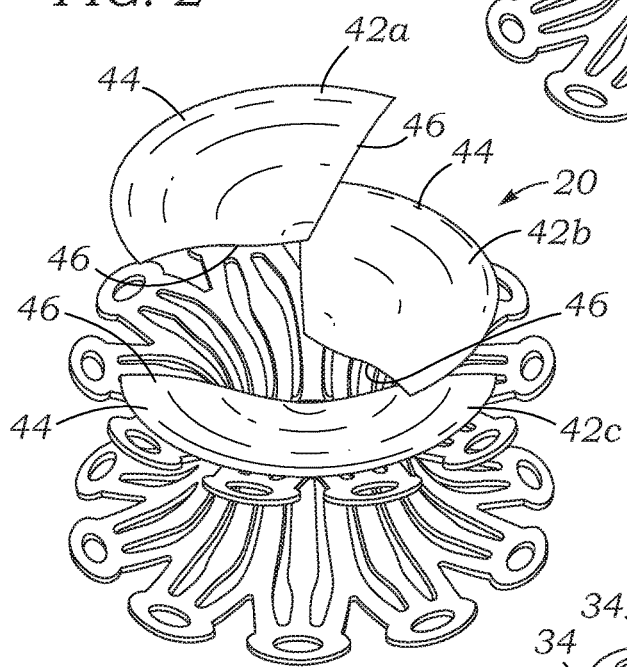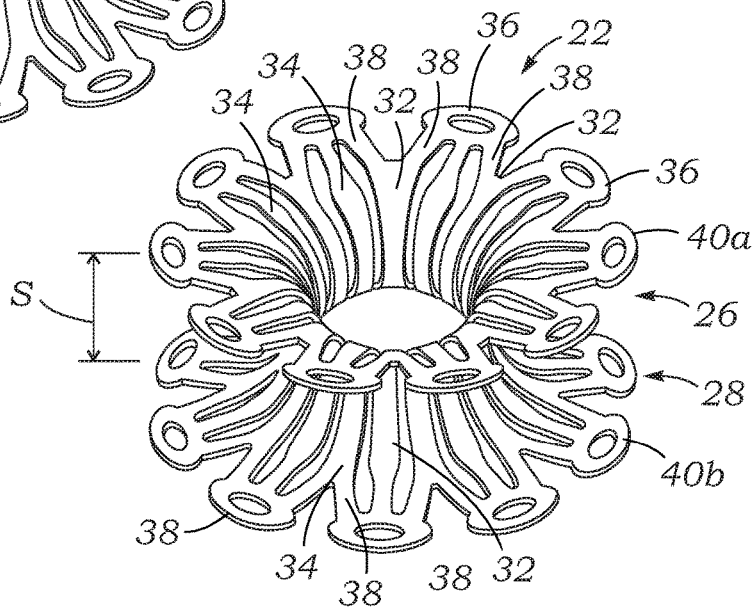

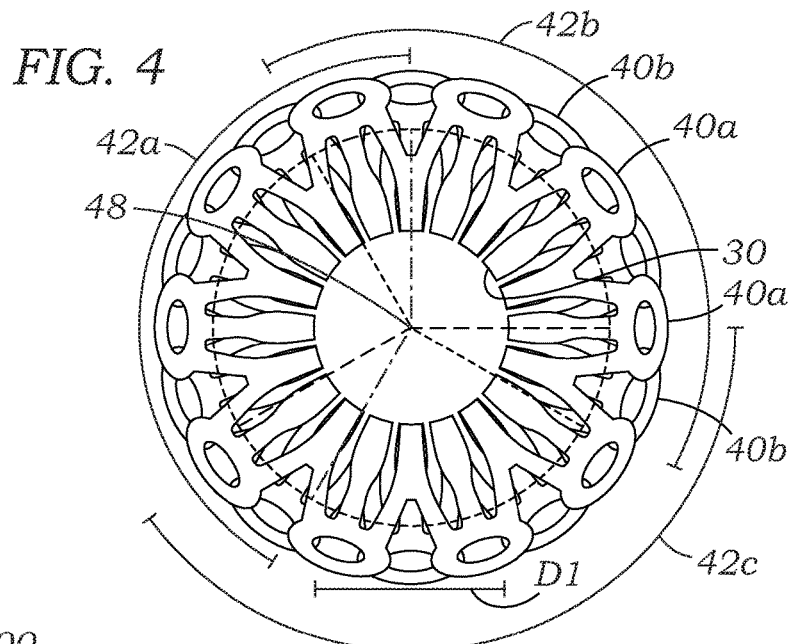
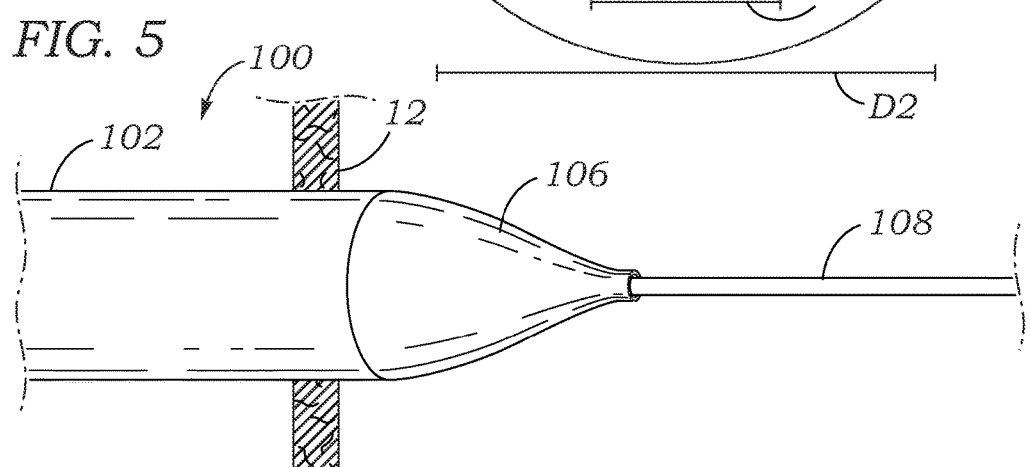
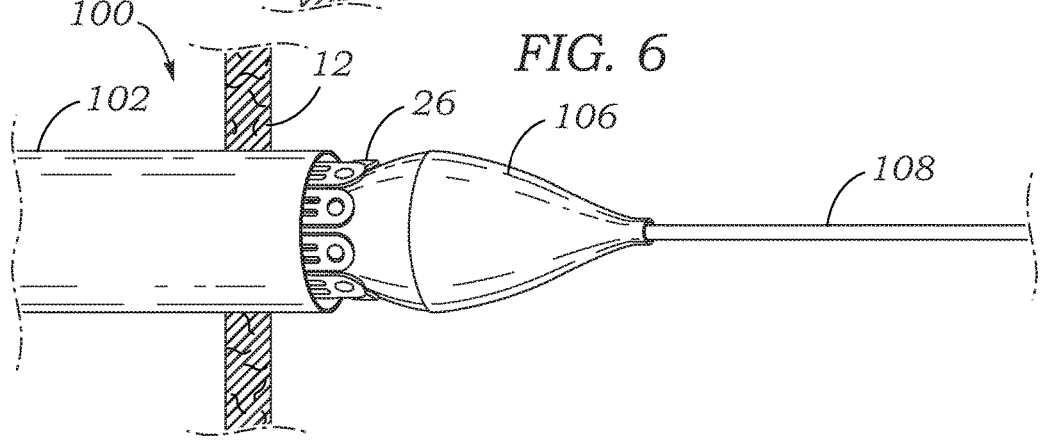

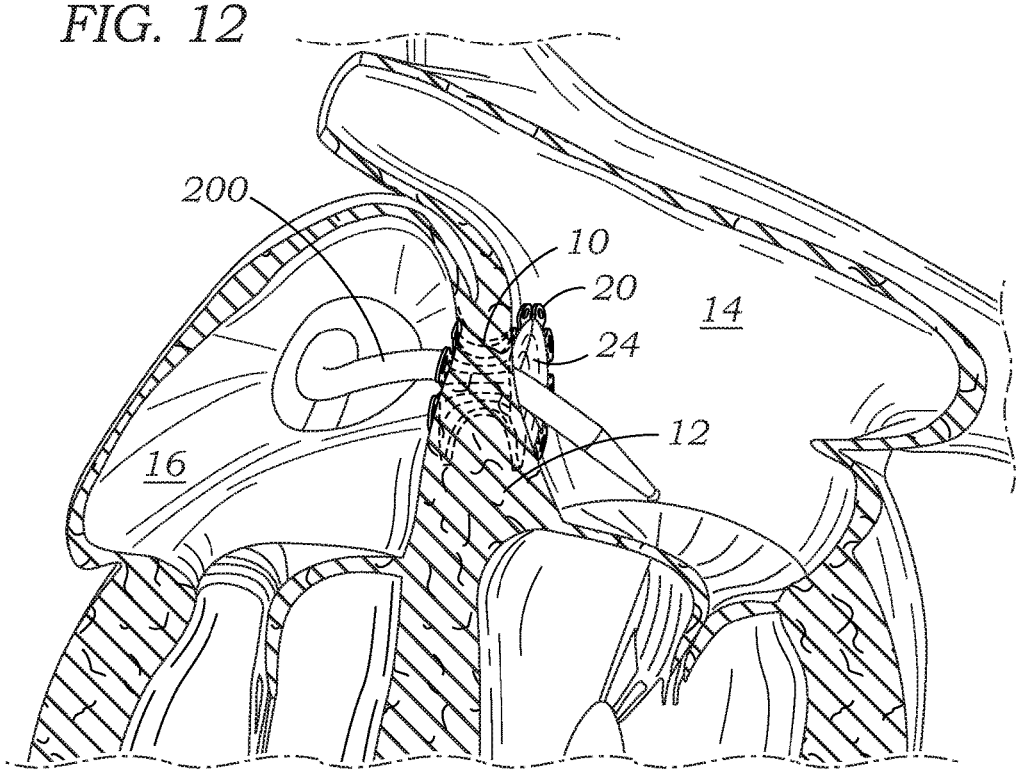
FIG. 12
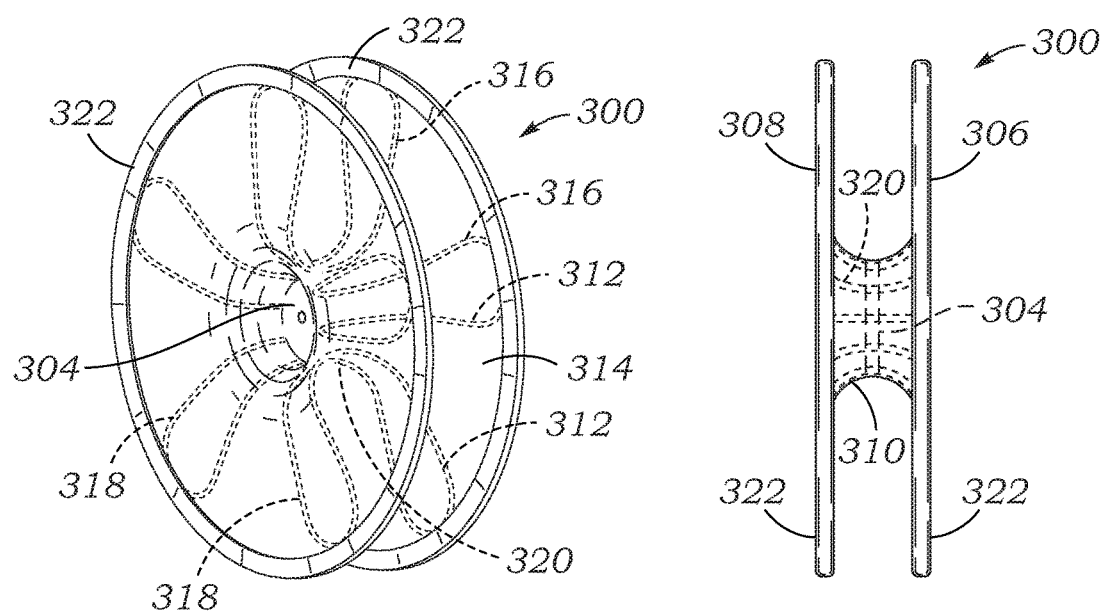
FIG. 13
FIG. 14

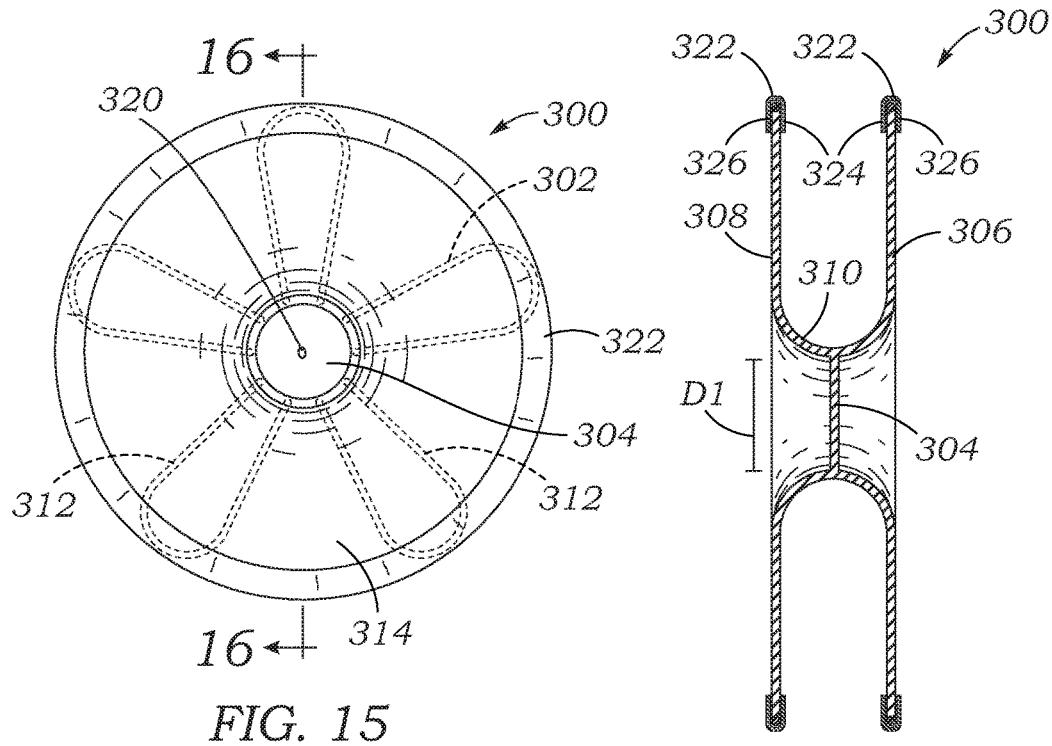
FIG. 15
FIG. 16
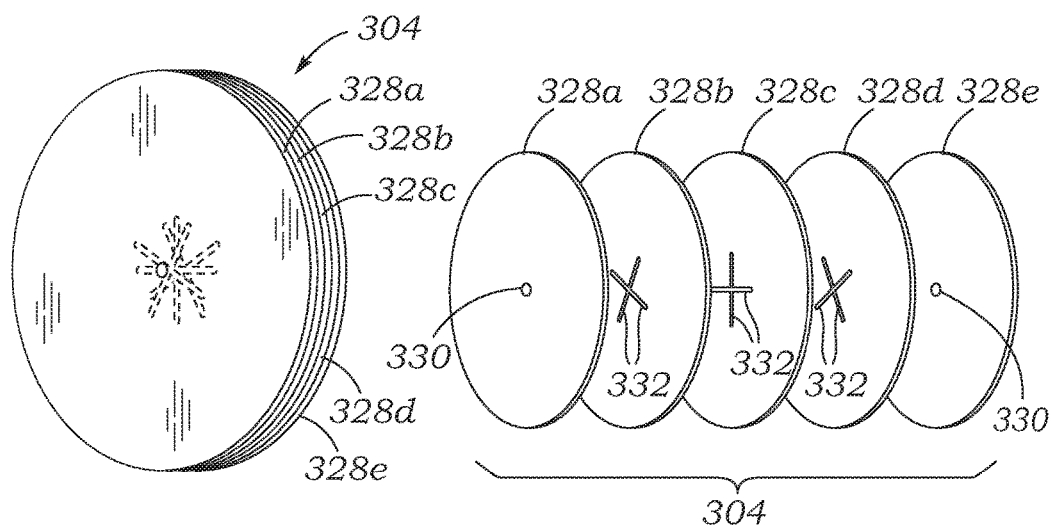
FIG. 17
FIG. 18

TRANS-SEPTAL CLOSURE AND PORT DEVICE

CROSS REFERENCE TO RELATED APPLICATION

This application claims the benefit of U.S. Provisional Patent Application No. 62/291,258, filed Feb. 4, 2016, which is incorporated herein by reference.

FIELD

The present disclosure relates generally to a method and device for closing a septal defect, or opening in the septum. In particular, the present disclosure relates to a method and device for closing a septal defect, for example a defect in an atrial septum, such that the septal defect can be accessed for reentry through the defect.

BACKGROUND

A septum may include a thin wall dividing a cavity into two smaller structures. An atrial septum is a wall of tissue separating the left and right atria of the heart. A ventricular septum is a wall of tissue separating the left and right ventricles of the heart. A septal defect may include a perforation or hole in the septum. A septal defect can occur congenitally or by puncturing the septum with a medical device to access a location within the heart.

The femoral artery is an access point for many catheterization laboratory procedures, with a smaller percentage of procedures utilizing venous or radial artery access. Likewise, the atrial septum is a point of percutaneous access for atrial fibrillation therapy, left atrial appendage closure, percutaneous mitral valve repair, and percutaneous mitral valve replacement. In these and other procedures, devices may traverse the atrial septum and, by doing so, may leave a defect or orifice in the atrial septum that cannot close or heal by itself. Therefore, these defects are often closed using devices, such as plugs. However, these devices do not allow for re-access through the septum. Thus a need exists for improved closure devices for closing a septal defect and for re-accessing the left side of the heart in subsequent procedures.

SUMMARY

In certain embodiments, the present disclosure describes a septal port device that is suitable for providing an access port to the left side of the heart with a catheter or other medical device. In certain embodiments, the port device is also suitable to close or repair a septal orifice while allowing for re-entry through a septum at the same septal orifice location at a later time as other therapeutic interventions are warranted.

In one representative embodiment, a septal closure and port device for implantation in the atrial septum of a patient's heart comprises an expandable frame comprising a central portion defining a lumen, and first and second opposing end portions extending from opposite ends of the central portion. The frame is configured to expand and contract between a compressed, tubular configuration for delivery through the patient's vasculature and an expanded configuration in which the first and second end portions extend radially outwardly from the opposite ends of the central portion and can compress the atrial septum there between. The device further comprises a valve member supported on the frame and positioned to block at least the flow of blood from the left atrium to the right atrium through the lumen of the frame. The valve member is configured to permit a medical instrument inserted in the right atrium to pass through the lumen and the valve member and into the left atrium, such as for performing a subsequent medical procedure in the left side of the heart, for example, implanting a prosthetic mitral valve.

In another representative embodiment, a medical procedure comprises inserting a delivery catheter into the vasculature of a patient, the delivery catheter comprising a sheath containing a septal closure and port device in a compressed configuration; advancing at least a distal end portion of the sheath across the atrial septum of the patient's heart; and deploying the closure and port device from the sheath such that a central portion of the closure and port device extends through an orifice in the atrial septum and first and second opposing end portions of the closure and port device are deployed on opposite sides of the septum, which is compressed between the first and second end portions. The closure and port device further comprises a valve member that blocks at least the flow of blood from the left to the right atrium through the central portion.

In some embodiments, the method can further comprise inserting a medical instrument through the valve member and performing a medical procedure in the left side of the heart using the medical instrument. In some embodiments, the medical instrument can comprise a delivery catheter and a prosthetic heart valve carried on a distal end portion of the delivery catheter, and performing a medical procedure comprises implanting the prosthetic heart valve in the native mitral valve annulus of the heart.

The foregoing and other objects, features, and advantages of the present disclosure will become more apparent from the following detailed description, which proceeds with reference to the accompanying figures.

BRIEF DESCRIPTION OF THE DRAWINGS

FIG. 1 is a perspective view of a septal closure and port device, according to one embodiment.

FIG. 2 is a perspective, exploded view of the closure and port device of FIG. 1.

FIG. 3 is a perspective view of the frame of the closure and port device of FIG. 1.

FIG. 4 is a front elevation view of the closure and port device of FIG. 1, as viewed from the proximal side of the device.

FIGS. 5-10 are side views of the distal end portion of a delivery apparatus shown at various stages of an implantation procedure for implanting the closure and port device of FIG. 1 in the atrial septum, according to one embodiment.

FIGS. 11-12 are cross-sectional views of the heart showing the closure and port device of FIG. 1 implanted in the atrial septum and a delivery apparatus crossing the closure and port device to perform a procedure in the left side of the heart.

FIG. 13 is a perspective view of a septal closure and port device, according to another embodiment.

FIG. 14 is a side view of the septal closure and port device of FIG. 13.

FIG. 15 is a front elevation view of the septal closure and port device of FIG. 13.

FIG. 16 is a cross-sectional view of the septal closure and port device of FIG. 13 taken along line 16-16 of FIG. 15.

FIG. 17 is a perspective view of the valve member of the septal closure and port device of FIG. 13 shown apart from the frame.

FIG. 18 is a perspective, exploded view of the valve member of FIG. 17.

DETAILED DESCRIPTION

Figure 7:
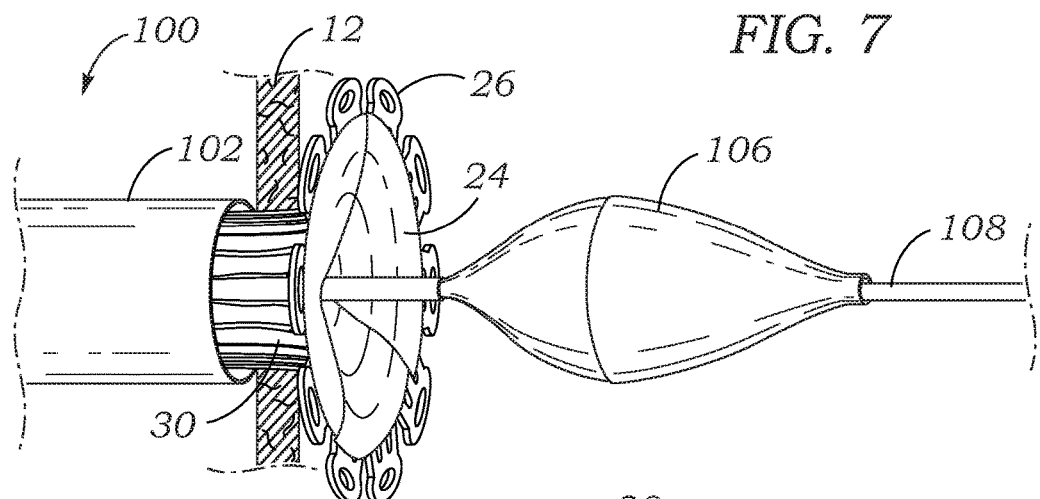

For purposes of this description, certain aspects, advantages, and novel features of the embodiments of this disclosure are described herein. Features, integers, characteristics, compounds, chemical moieties or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations wherein at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

In certain embodiments, the present disclosure describes a septal port device that is suitable for providing an access port to the left side of the heart with a catheter or other medical device. In certain embodiments, the port device is also suitable to close or repair a septal orifice while allowing for re-entry through a septum at the same septal orifice location at a later time as other therapeutic interventions are warranted. As used herein, the term "septal orifice" or "orifice" is used to describe an orifice created by puncturing the septum with a catheter or other medical device and an orifice that occurs congenitally, such as an atrial septal defect (ASD) or a patent foramen ovale (PFO).

FIG. 12 illustrates a heart shown in cross section having a septal orifice 10 in an atrial septum 12 between a left atrium 14 and a right atrium 16. In the illustrated embodiment, the orifice 10 is created by puncturing the septum 12 with a catheter, as described in detail below, for example, to repair or replace a valve or other tissue in the left side of the heart. An exemplary port device 20 for implantation in the septal orifice 10 is illustrated in FIGS. 1-4.

The port device 20 can include a frame 22 configured to support a membrane or valve member 24. The frame 20 can generally comprise a first end portion 26, a second end portion 28, and a central portion 30 between the first and second end portions. In its deployed state, the first and second end portions 26, 28 can extend radially outwardly from the central portion 30 (as shown in FIGS. 1-4), thereby forming opposing flange portions of the frame 22. The first and second end portions 26, 28 can extend perpendicularly or substantially perpendicularly to the central axis of the device (the central axis extending through the lumen from the first end to the second end of the device) to compress or pinch the atrial septum between the end portions 26, 28 when the device is implanted in the atrial septum.

The frame 22 can be radially compressed or constricted to a delivery configuration for delivery to the heart on a delivery apparatus, as shown in FIG. 6. In the delivery configuration, the frame 22 can be placed and retained in a generally cylindrical or tubular configuration in which the first and second end portions 26, 28 are folded toward the central axis of the device such that they extend axially and parallel to each other and the central portion 30. When placed in the delivery configuration, the frame 22 can also be radially compressed relative to the deployed configuration such that the lumen of the frame has a reduced diameter relative to the diameter of the lumen in the deployed configuration.

The frame 22 can be self-expandable and can be formed from a shape-memory material, such as Nitinol, so that the frame 22 self-expands from the delivery configuration to the deployed configuration when released or deployed from a delivery apparatus. In alternative embodiments, the frame 22 can be formed from a plastically-expandable material, such as stainless steel or cobalt-chromium alloy, and can be configured to be plastically expanded from the delivery configuration to the deployed configuration by an expansion device, such as an inflatable balloon.

The frame 22 in the illustrated embodiment comprises a plurality of alternating struts 32, 34 extending between nodes or connecting portions 36 (also referred to as apices) at the opposing ends of the frame. A plurality of angularly spaced fingers 40a and 40b can be formed at the first and second end portions 26, 28, respectively, of the frame by the struts 32, 34 and nodes 36. As best shown in FIG. 4, the fingers 40a, 40b can be angularly offset from each other such that the fingers 40a at the first end portion 26 of the frame are positioned circumferentially between the fingers 40b of the second end portion 28 of the frame. Advantageously, this configuration can provide a greater retaining or clamping force against the tissue surrounding the orifice 10.

As best shown in FIG. 3, at the first end portion 26 of the frame, the end of each strut 34 can be connected directly to a respective node 36, and at the second end portion 28 of the frame, the end of each strut 34 can be connected to two diverging secondary struts 38, which in turn can be connected to respective adjacent nodes 36. Similarly, at the second end portion 28 of the frame, the end of each strut 32 can be connected directly to a respective node 36, and at the first end portion 26 of the frame, the end of each strut 32 can be connected to two diverging secondary struts 38, which in turn can be connected to respective adjacent nodes 36. In this manner, the fingers 40a, 40b arranged offset relative to each other as shown in FIG. 4. In the illustrated embodiment, there are ten fingers 40a, 40b at each end of the frame 22. The nodes 36 can have a circular shaped as shown, although other shapes can be used. In alternative embodiments, the struts 32, 34, 38 and nodes 36 can be arranged such that the fingers 40a, 40b are angularly aligned with one another.

As shown in FIG. 4, the frame 22 in the deployed configuration can include an inner diameter (D1) and an outer diameter (D2). The inner diameter D1 can be slightly less to slightly greater than that the diameter of the orifice 10 in the septum 12. The outer diameter D2 can be defined by the circumference formed from the ends of the fingers 40a, 40b. The number of fingers 40 at each end of the frame, the length of the fingers, and the inner and outer diameter of the frame can be varied as needed for particular applications of the puncture frame.

In certain embodiments, the inner diameter (D1) can be between about 5 mm and 15 mm, and more specifically, between about 6 mm and 12 mm, with 10 mm being a specific example. The outer diameter (D2) can be between about 12 mm and 36 mm, and more specifically, between about 20 mm and 30 mm, with 30 mm being a specific example. The maximum spacing or width (S) (FIG. 3) between the outer ends of the fingers 40a, 40b can be between about 1 mm and 10 mm, and more specifically, between about 2 mm and 8 mm, with 3 mm being a specific example.

The valve member 24 can be configured to block the flow of blood between the right and left atria through the port device 20 but permit passage of a medical device through the lumen of the port device. For an adult, the normal range of right atrial pressure (RAP) is about 2-6 mmHg and the normal range of left atrial pressure (LAP) is about 4-12 mmHg. Thus, throughout most of the cardiac cycle, the LAP is greater than the RAP. In some embodiments, the valve member 24 can be configured to block at least the flow of blood from left atrium to the right atrium. In other embodiments, the valve member 24 can be configured to block the flow of blood between the right and left atria in both directions throughout the cardiac cycle.

The valve member 24 in the illustrated embodiment comprises a plurality of overlapping "leaflets" or flaps 42a, 42b, 42c that are arranged relative to each other to maintain a closed position against a blood pressure gradient between the right atrium 16 and the left atrium 14 but can be opened by the force of a catheter or other medical instrument to permit passage of the medical instrument through the lumen of the port device 20. The flaps primarily block the flow of blood from the left atrium to the right atrium due to the typically higher LAP, but can also block the flow of blood from the right atrium to the left atrium if the RAP exceeds the LAP. The plurality of overlapping flaps 42a, 42b, 42c can also be described as forming an expandable hole 48, the hole 48 having a closed configuration to block at least the flow of blood from the left atrium to the right atrium through the hole 48 and an expanded configuration to permit a medical instrument inserted in the right atrium to pass through the lumen and the valve member and into the left atrium.

Each flap 42a-42c can comprise an angular wedge-shaped or pie-shaped segment comprising an outer peripheral edge portion 44 and radially extending side edge portions 46. The flaps 42a-42c can be secured to the first end portion 26 of the frame 22 using suitable techniques or mechanisms known to those skilled in the art with the benefit of the present disclosure. For example, outer peripheral edges 44 of the flaps 42a-42c can be secured to the fingers 40a, such as with sutures, an adhesive, and/or welding. As depicted in FIG. 4, each of the radially extending edge portions 46 of a flap can overlap an adjacent edge portion 46 of an adjacent flap. FIG. 4 shows the arc length of each flap and depicts each flap in a different line pattern to show the overlapping relationship of the flaps. Also, the radially extending edge portions 46 of the flaps can be unattached to the frame 22 and to each other. In some embodiments, the radially extending side edge portions 46 can be secured to each other or to the frame proximate the outer peripheral edge portions 44 so long as the flaps can be opened by the force of a medical instrument inserted through the lumen of the device.

Although three flaps 42a-42c are shown in the illustrated embodiment, a greater or fewer number of flaps can be used in alternative embodiments. Also, the flaps 42a-42c can be equally sized and shaped, while in other embodiments the flaps can comprise different sized angular segments. In particular embodiments, for example, each flap comprises an angular segment that has an angle greater than 90 degrees between the radially extending sides, such as about 100 to 120 degrees. In other embodiments, each flap 42a-42c can subtend a different angle between the radially extending sides.

The flaps 42a-42c can be formed from any of various suitable materials, including natural tissue or synthetic materials, such as any of various woven (e.g., fabric) or non-woven materials made from any of various polymeric materials. Some examples of natural tissue include, for example, bovine, porcine, or equine pericardial tissue or pericardial tissue from other animals. Some examples suitable polymeric materials include, for example, polyurethane or polyester. In one specific example, the flaps can comprise polyethylene terephthalate (PET) fabric.

The port device 20 in the illustrated embodiment includes a valve member 24 mounted to the first end portion 26 of the frame 22. In alternative embodiments, a valve member 24 can be mounted to the second end portion 28 of the frame or to both the first and second end portions 26, 28 of the frame. In other embodiments, a valve member 24 can be mounted within the central portion 30 of the frame.

In alternative embodiments, valve members having different constructions can be incorporated in the port device 20. In one implementation, for example, a valve member can comprise a slit valve comprising one of more layers of material with each layer of material having a slit or opening formed at its center to permit passage of a medical device (e.g., as shown in the embodiment of FIGS. 13-18, described below) and prevent or minimize the flow of blood through the valve member when the medical device is removed. In still alternative embodiments, the valve member 24 can comprises one or more metal struts pivotally connected to the frame 22 (e.g., to the central portion 30 of the frame such as by hinges) and covered with a blood-impermeable material, such as a woven or non-woven polymeric material or natural tissue. The metal struts can be biased to maintain a closed position blocking the flow of blood between the right and left atria (in one or both directions) but can be pushed open by the force of the distal end of a medical instrument inserted through the lumen of the port device.

In some embodiments, the port device 20 can include a cover or skirt that covers the metal struts of the frame or selected portions of the metal struts, such as to promote tissue in-growth. The cover can be formed from any of various suitable materials, including natural tissue or synthetic materials, such as any of various woven (e.g., fabric) or non-woven materials made from any of various polymeric materials, including any of the materials discussed above in regards to the flaps 42a-42c of the valve member (e.g., PET fabric). As discussed in detail below in connection with the embodiment of FIGS. 13-16, the cover can comprise strips of fabric or another suitable material placed only along the outer peripheral edges of the first and second end portions 26, 28 of the frame to promote tissue in-growth at those locations of the frame.

FIGS. 5-9 illustrate one example of delivering and implanting the port device 20 using an exemplary delivery apparatus 100. The delivery apparatus 100 can generally comprise an outer sheath 102, an inner shaft 104 (FIG. 8) extending co-axially through the outer sheath 102, and a nose cone 106 mounted to the distal end portion of the inner shaft 104. The inner shaft 104 and the nose cone 106 can include a lumen sized to allow the delivery apparatus 100 to be advanced over a guidewire 108. The proximal ends of the sheath 102 and the inner shaft 104 can be coupled to a handle (not shown) having appropriate actuators (e.g., knobs) to effect relative longitudinal movement of the outer sheath 102 and the inner shaft 104.

Prior to implantation, the port device 20 can be radially compressed to the delivery configuration and loaded into the distal end portion of the sheath 102. The delivery apparatus 100 can be advanced percutaneously through the patient's vasculature to the right atrium 16 of the heart in a trans-septal, antegrade approach for implanting the port device 20 in the septum 12. In one approach, the delivery apparatus 100 can be advanced through a femoral vein, the inferior vena cava, and into the right atrium. In another approach, the delivery apparatus can be advanced through a vein of the upper torso (e.g., a jugular vein), the superior vena cava, and into the right atrium.

Once in the right atrium, the delivery apparatus 100 can be advanced through the septum 12 to position the nose cone 106 and a distal end portion of the sheath 102 in the left atrium 14, as shown in FIG. 5. If there is an existing orifice 10 in the septum (e.g., from a congenital defect), the delivery apparatus 100 can be advanced through the orifice 10. If the port device 20 is being used to provide an access port in a healthy septum to perform a procedure on the left side of the heart, the guidewire 108 and/or the nose cone 106 can be used to puncture the septum 12 and create an orifice 10.

Figure 8:
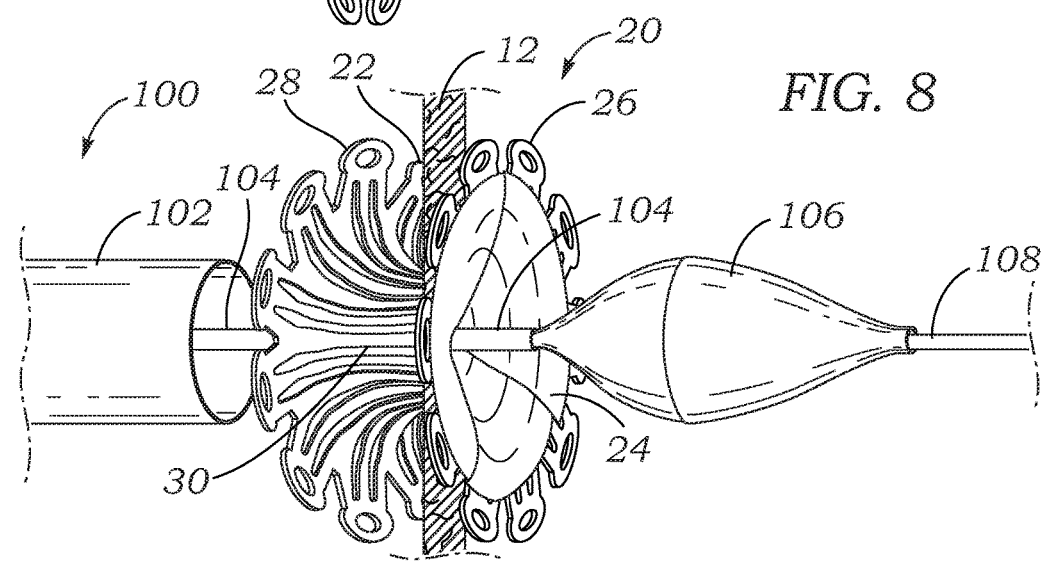

As shown in FIGS. 6 and 7, the sheath 102 can then be retracted proximally to deploy the first end portion 26 of the port device, allowing the first end portion 26 to radially expand. The inner shaft 104 and the nose cone 106 can be advanced distally during deployment of the first end portion 26. The entire delivery apparatus 100 can then be retracted slightly to bring the expanded first end portion 26 against the septum 12 within the left atrium, as shown in FIG. 7. Thereafter, as shown in FIG. 8, the sheath 102 can be further retracted to deploy the central portion 30 and the second end portion 28, allowing the second portion 28 to radially expand against the septum 12 in the right atrium, leaving the port device 20 implanted in the orifice 10 in the septum. The clamping force of the fingers 40a, 40b against the opposing sides of the septum can retain the port device in the orifice.

Figure 9:
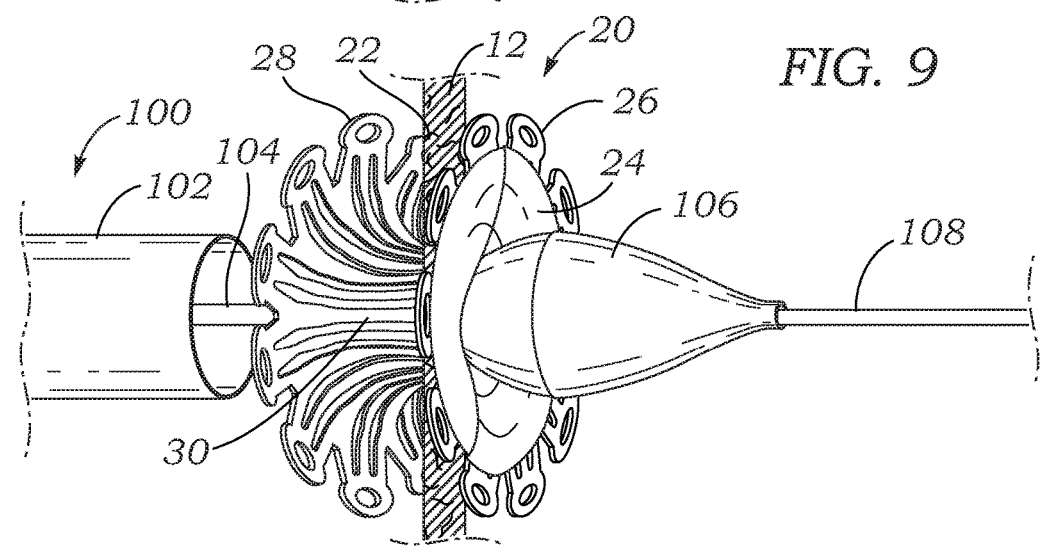
Figure 10:
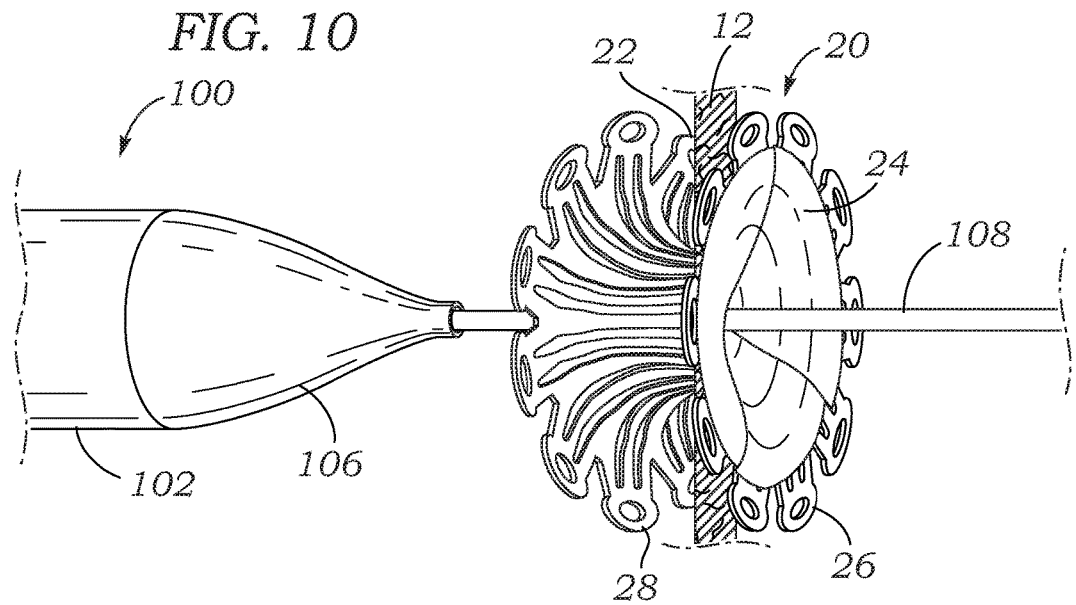

Following deployment, as shown in FIGS. 9-10, the nose cone 106 can be retracted back through the valve member 24 and the central portion 30 of the port device 20 to mate with the distal end of the sheath 102, after which the delivery apparatus 100 can be removed from the patient's body. As discussed above, when the delivery apparatus is removed, the valve member 24 can move to a closed position to block the flow of blood between the right atrium and the left atrium. The guidewire 108 can be left in place if another medical instrument is to be used to access the left side of the heart in a subsequent procedure.

Figure 11:
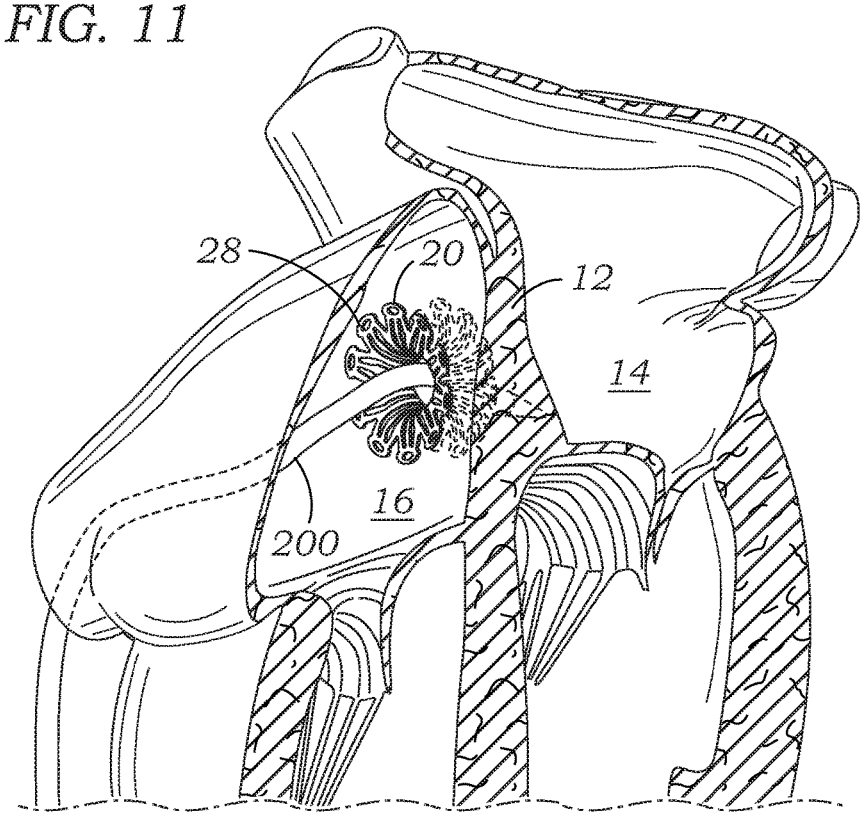

FIGS. 11 and 12 are two cross-sectional views of the heart showing another delivery apparatus 200 being advanced through the port device 20 to access the left side of the heart in a trans-septal procedure. FIGS. 11 and 12 show the delivery apparatus 200 extending through the inferior vena cava into the right atrium 16 and through the valve member 24 of the port device 20. The flaps 42a-42c can form a seal around the outer surface of the delivery apparatus 200 to prevent or at least minimize blood flow through the port device 20 when the delivery apparatus extends through the valve member 24. It can be appreciated that the path of the delivery apparatus 200 shown in FIGS. 11 and 12 also represents the delivery path of the delivery apparatus 100 when advanced trans-septally to the heart via the inferior vena cava.

A conventional trans-septal delivery technique of a catheter designed to puncture the septum 12 may involve pushing the catheter such that a portion of the catheter leans against the right atrial wall until its distal end "falls" into or engages the fossa ovalis dent in the right atrial side of the septum, which is the desired puncture site on the septum. The port device 20 mimics the native anatomy of the septum in that the central portion 30 forms a dent relative to the second portion 28 of the frame to facilitate crossing of the port device using a conventional trans-septal medical instrument. The struts 32, 34 can curve as they transition from the end portions of the frame to the central portion 30, which helps guide the distal end of a medical instrument through the port device as the medical instrument is pushed through the right atrium.

The delivery apparatus 200 can be, for example, a delivery apparatus for delivering and implanting a prosthetic heart valve in the native mitral valve or the native aortic valve. In alternative embodiments, the delivery apparatus 200 can be used to deliver and implant various other prosthetic devices in the left atrium, mitral valve, left ventricle, and/or the aortic valve, including, for example, annuloplasty rings, closure devices for the left atrial appendage, sealing devices or reshaping devices for repairing or reshaping portions of the heart. In other embodiments, other percutaneous medical instruments can be advanced through the port device 20 for performing a procedure on the left side of the heart, such as atrial fibrillation therapy.

FIGS. 13-16 show a port device 300, according to another embodiment. The port device 300 generally comprises a frame 302 and a valve member 304 supported by the frame 302. In its deployed configuration, the frame 302 can generally comprise first and second flange portions 306, 308, respectively, extending radially outwardly from a central portion 310. Similar to the port device 20 described above, the port device 300 can be radially collapsed to a tubular delivery configuration and placed inside the sheath of a delivery apparatus for delivery and implantation in the atrial septum 12.

The frame 302 can comprise a plurality of frame members 312 that can be encapsulated by an encapsulating layer 314.

Each frame member 312 can comprise an enclosed wireform structure that extends from one end of the port device 300 to the other end of the port device 300. First end portions 316 of the frame members 312 form a first set of radially extending fingers and second end portions 318 of the frame members 312 form a second set of radially extending fingers. The first flange portion 306 thus can be formed by the first fingers 316 and the portion of the encapsulating layer 314 encapsulating the first fingers 316. Similarly, the second flange portion 308 can be formed by the second fingers 318 and the portion of the encapsulating layer 314 encapsulating the second fingers 318. The central portion 310 of the frame 302 can be formed from intermediate portions 320 of the frame members 312 and the portion of the encapsulating layer 314 encapsulating the intermediate portions 320.

In the illustrated embodiment, the frame members 312 are discrete frame members that are not interconnected to each other with metal struts or other metal frame members. This allows the central portion 310 to more easily expand radially to accommodate a relatively larger medical instrument inserted through the port device 300, as further described below. In other embodiments, the frame 302 can include metal struts or frame members interconnecting the frame members 312.

The encapsulating layer 314 can be made of any suitable biocompatible material. In one example, the encapsulating layer 314 can be formed using an electrospinning process. In other examples, the encapsulating layer 314 can be formed using any other suitable method including, for example, dip coating, spray coating, or melt-spinning. The biocompatible material may be a non-absorbable polymeric material (i.e., a material that does not dissolve once implanted in the body), preferably an elastomer. The material for forming the encapsulating layer 314 can be selected to prevent or minimize tissue in-growth and integration of the port device with adjacent tissue. Examples of suitable materials include, without limitation, polytetrafluoroethylene (PTFE), polyethylene (e.g., ultrahigh molecular weight polyethylene (UHMWPE)), silicones (e.g., silicone rubber), polyurethane, or various combinations of any of these materials. In some embodiments, the encapsulating layer can be treated or can be coated with an outer layer to induce some tissue in-growth with the flanges 306, 308.

In particular embodiments, the encapsulating layer 314 can comprise a first, inner layer and a second, outer layer formed from respective tubes made of a suitable polymeric material (e.g., PTFE tubes or UHMWPE tubes). The frame members 312 can be placed co-axially between the inner and outer layers, which can then be bonded to each other when subjected to heat and/or pressure treatment to form a laminate.

The frame 302 can further include fabric or cloth strips 322 covering the outer peripheral edge portions of the first and second flanges 306, 308. As best shown in FIG. 16, each strip 322 can be wrapped around a peripheral edge portion of a flange 306, 308 so as to form an inner layer 324 on the inside of the flange and an outer layer 326 on the outside of the flange. The strips 322 can be formed from any of various suitable biocompatible fabrics, such as PET. The strips 322 can be secured to the frame 302, for example, by suturing the strips 322 to the frame members 312 and/or the encapsulating layer 314. The strips 322 promote tissue in-growth of the port device 300 only along the peripheral edge portions of the flanges 306, 308.

The valve member 314, like the valve member 24, can be configured to retain a closed configuration when a medical instrument is not inserted through the valve member in order to block blood flow between the right and left atria in both directions. As best shown in FIGS. 17-18, the valve member 314 in the illustrated embodiment can comprise one or more layers of disc-shaped valve elements 328a, 328b, 328c, 328d, 328e stacked against each other. Although five valve elements 328a-328e are used in the illustrated embodiment, the valve member 314 can have fewer or greater number of valve elements 328. The valve elements can be made of a biocompatible polymeric material and/or elastomer, such as any of the materials mentioned that can be used to form encapsulating layer 314. As best shown in FIG. 16, the valve member 314 can be supported at the center of the lumen of the central portion 310 of the frame 302. The valve member 314 can be secured to the frame 302, for example, by welding, an adhesive, and/or sutures.

Each valve element 328a-328e can include an aperture or slit to permit passage of a medical instrument through the valve member 314. In some embodiments, the aperture or slit can be expandable. In the illustrated embodiment, for example, the outer valve elements 328a, 328e can be formed with centrally located apertures 330, while the inner valve elements 328b, 328c, 328d can be formed with slits or cuts 332, such as cross-shaped or x-shaped slits as shown.

The slits 332 of adjacent valve elements can be angularly or rotationally offset from each other to enhance sealing of the valve member 314 in a closed state. For example, the slits 332 of the central valve element 328c can be rotationally offset from the slits 332 of the valve element 328b by about 90 degrees, and the slits 332 of the valve element 328d can be rotationally offset from the slits 332 of the central valve element 328c by about 90 degrees. The outer valve elements 328a, 328e can be formed with apertures 330 rather than slits to prevent fluttering or movement of the flaps of the inner valve elements 328b, 328c, 328d against a blood pressure gradient across the valve member 314. In some embodiments, the aperture/slits of each valve element can be radially offset with respect to the aperture/slits of an adjacent valve element to further enhance sealing of the valve member in the closed state. For example, one valve element can have an aperture/slits located at the center of the valve element while an adjacent valve element can have an aperture/slits offset from the center of the valve element.

The port device 300 can be implanted in an orifice 10 of a septum 12 using the delivery apparatus 100 and methods described above in connection with the port device 20. The spacing between the flanges 306, 308 is selected such that the flanges provide a pinching or compression force against opposing sides of the septum 12 to anchor the port device 300 in place. After implantation in the septum, additional medical instruments (e.g., a delivery apparatus 200) can be inserted through the port device to perform a subsequent procedure on the left side of the heart.

The valve elements 328a-328e can form a seal around a medical instrument (e.g., a delivery catheter) inserted through the apertures/slits of the valve elements to prevent blood flow between the right and left atria during a subsequent medical procedure. As described above, the central portion 310 of the port device 300 can expand radially when the medical instrument is passed through the port device 300. Thus, the inner diameter D1 (FIG. 16) of the central portion 310 can be smaller than the outer diameter of a medical instrument that would be inserted through the port device 300 in a subsequent procedure.

As described above, the material used to form the encapsulating layer 314 can be selected to prevent or minimize tissue in-growth with the contacting faces of the flanges 306, 308 (the faces or surfaces of the flanges contacting the septum). If the flanges 306, 308 have fabric strips 322 along their peripheral edges, there can be relatively less tissue in-growth (or no tissue in-growth) across the central surface area of the flanges bounded by the strips 322 compared to the tissue in-growth that occurs along the strips 322. Thus, in particular embodiments, the majority of the surface area of the contacting faces of the flanges 306, 308 promotes little or no tissue in-growth. Minimizing the tissue in-growth across the surface area of the flanges 306, 308 is advantageous in that it minimizes stress on the tissue of the septum 12 when a medical instrument inserted through the port device causes expansion of the port device.

In alternative embodiments, any of the embodiments disclosed herein can be configured to function primarily as a closure device and not necessarily to facilitate multiple re-access through the septum. For example, the valve members 24, 304 of devices 20, 300 can be replaced with a flow-blocking member, such as sheet of fabric or tissue (e.g. pericardium), that blocks the flow of blood through the device but is not moveable or formed with any openings to permit passage of a medical instrument there through.

In some embodiments, the flow-blocking member can be punctured with a medical instrument if access through the septum is needed in a subsequent procedure. If the medical instrument has a relatively small diameter, such as used for treating arrhythmias, the hole formed in the flow-blocking member may be small enough to sufficiently inhibit blood flow between the left and right atria without further intervention. If the medical instrument has a relatively large diameter, such as a delivery apparatus for implanting prosthetic valve, and leaves a relatively larger opening in the flow-blocking member, another port and/or closure device can be implanted within the first closure device to block blood flow between the right and left atria.

Figure 19:
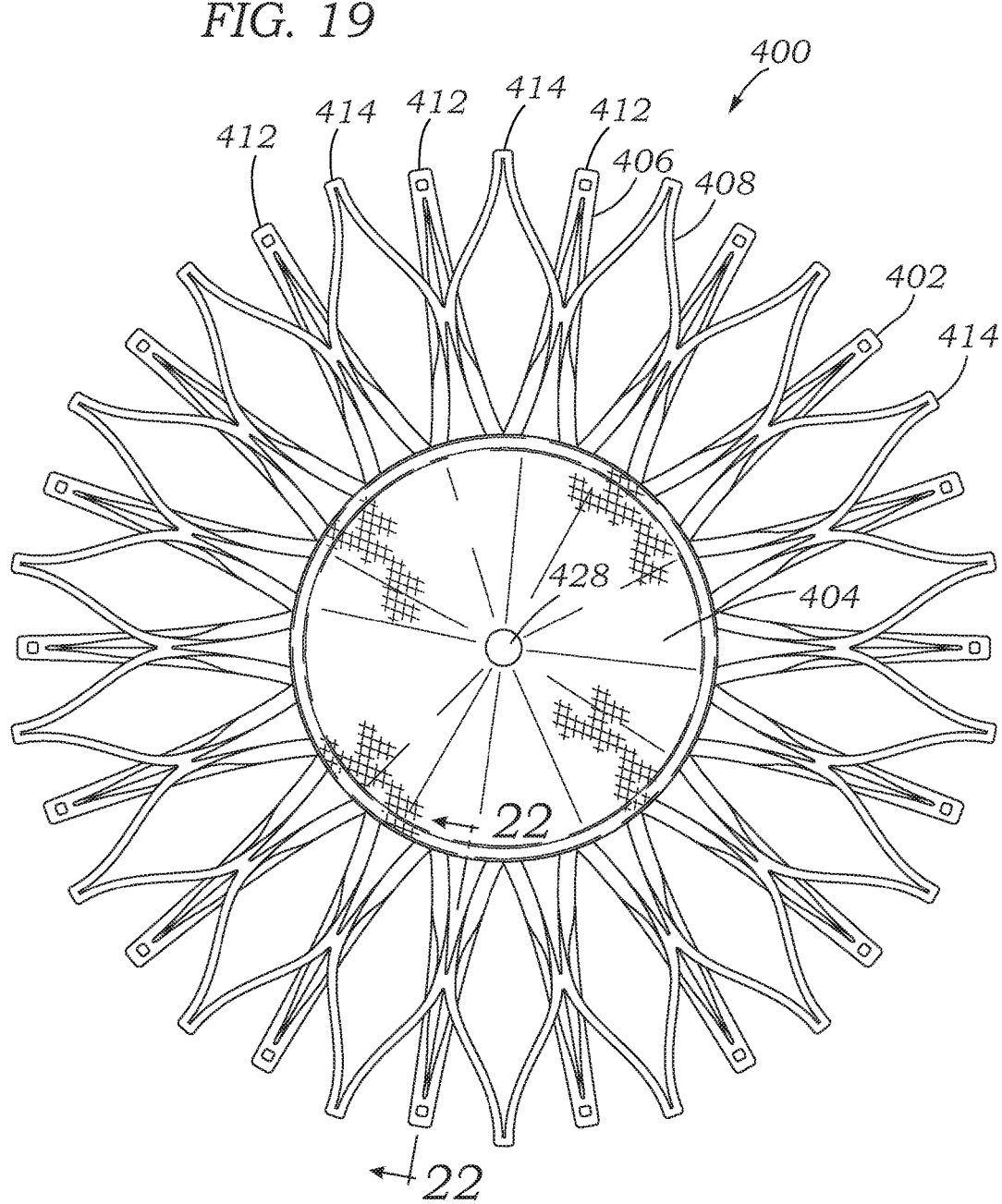
FIG. 19 is a front view of a septal closure and port device, according to another embodiment.
Figure 20:
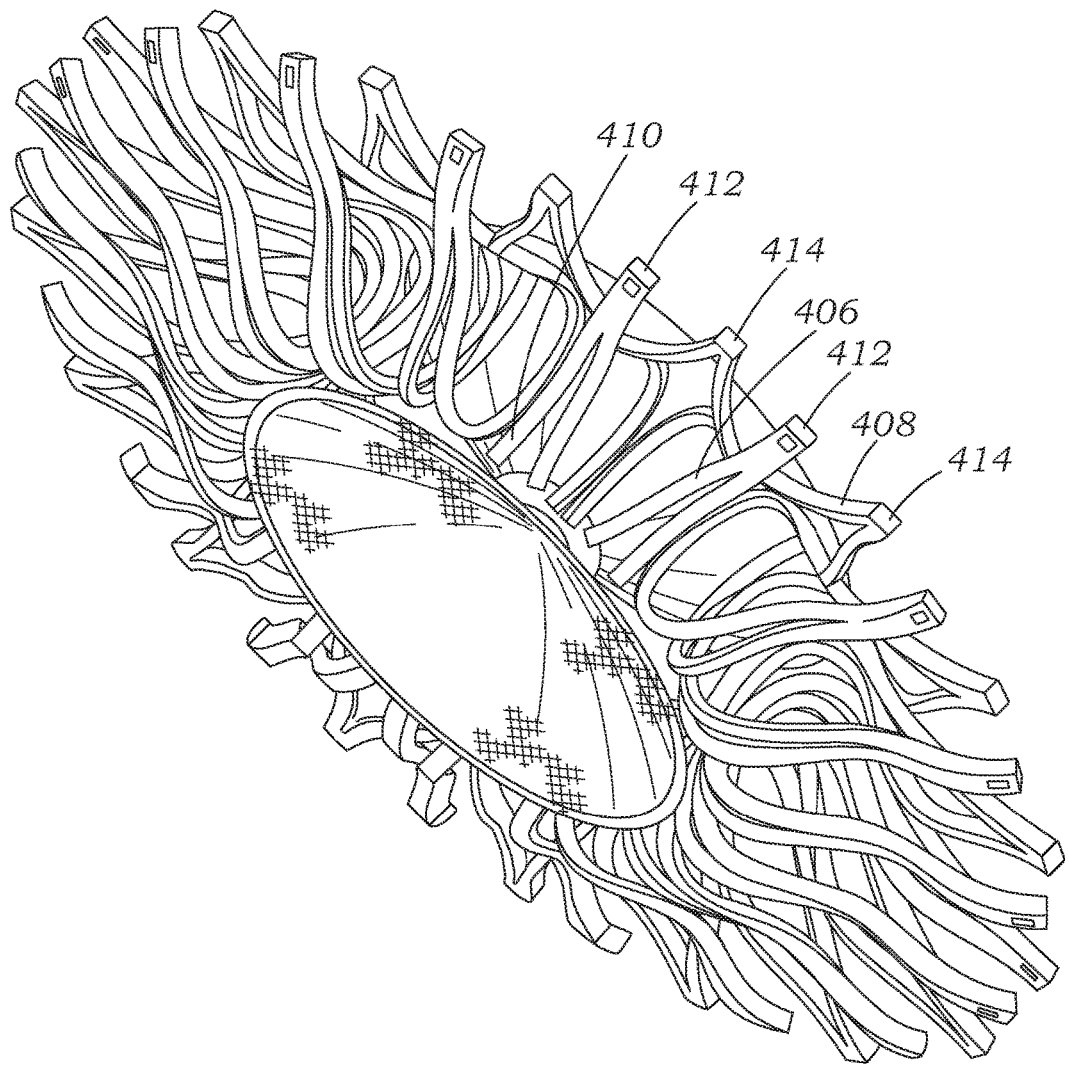
FIG. 20 is a side perspective view of the septal closure and port device of FIG. 19.

FIGS. 19-20 show a port device 400, according to another embodiment. The port device 400 generally comprises a frame 402 and a valve member 404 supported by the frame 402. In its deployed configuration, the frame 402 can generally comprise first and second portions 406, 408, respectively, extending radially outwardly from a central portion 410. Similar to the port device 20 described above, the port device 400 can be radially collapsed to a tubular delivery configuration and placed inside the sheath of a delivery apparatus for delivery and implantation in the atrial septum 12. When implanted, a resilient band member 424 of the valve member 404 may lie approximately in the plain of the septum 12.

The frame 402 in the illustrated embodiment comprises a wire form shape including a plurality of angularly spaced fingers 412 and 414 formed at the first and second end portions 406, 408, respectively, of the frame. As best shown in FIG. 20, the fingers 412, 414 can be angularly offset from each other such that the fingers 412 at the first end portion 406 of the frame are positioned circumferentially between the fingers 414 of the second end portion 408 of the frame. Advantageously, this configuration can provide a greater retaining or clamping force against the tissue surrounding the orifice 10. In alternative embodiments, frame 402 can be arranged such that the fingers 412, 414 are angularly aligned with one another.

Figure 22:
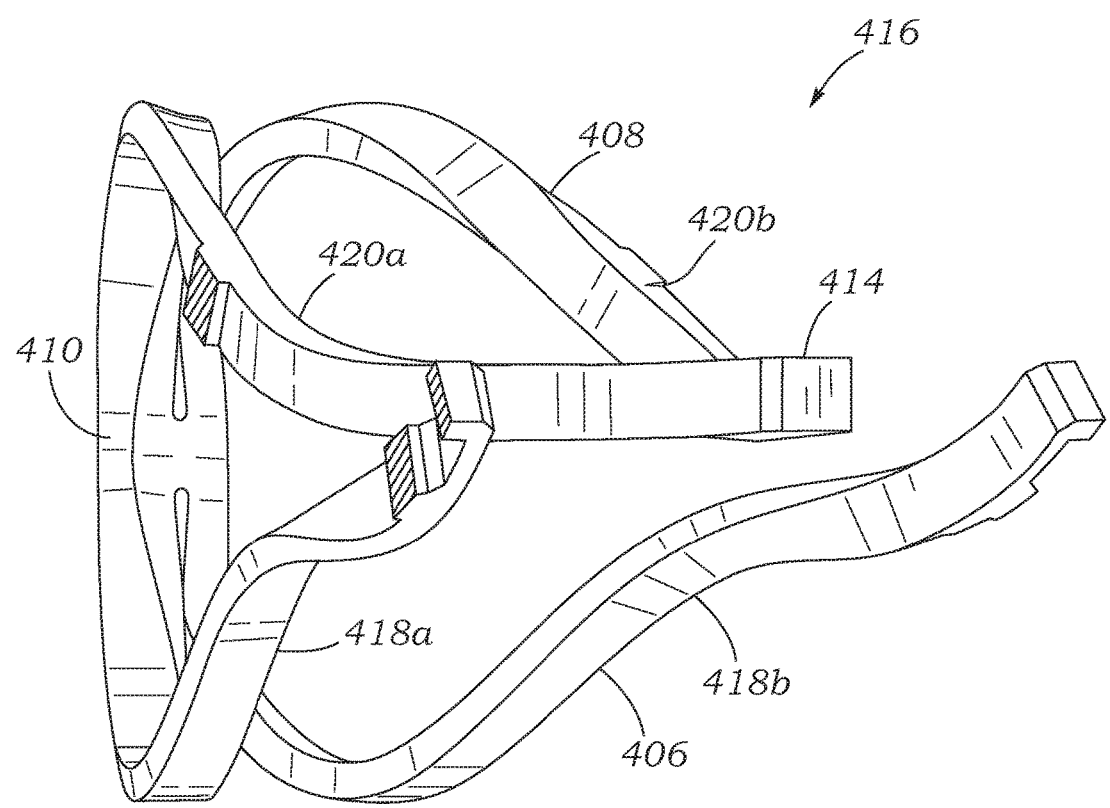
FIG. 22 is a side perspective view of a segment of the frame of the septal closure and port device of FIG. 19.

As best shown in FIG. 22, the frame 402 can also be described as comprising a plurality of connected segments 416 connected side-by-side to form a ring structure. Each segment 416 can include a section of the first end portion 406, the second end portion 408 and the central portion 410. The second end portion 408 can comprise two wire forms 420a and 420b extending from the central portion 410, the two wire forms 420a and 420b curving away then towards one another to form one of the fingers 414. The first end portion 406 can comprise two wire forms 418a and 418b extending from the central portion 410, the two wire forms 418a and 418b extending away from one another. One of the ends of the two wire forms 418a and 418b can be joined with an end of another segment 416 to form one of the fingers 412.

Figure 21:
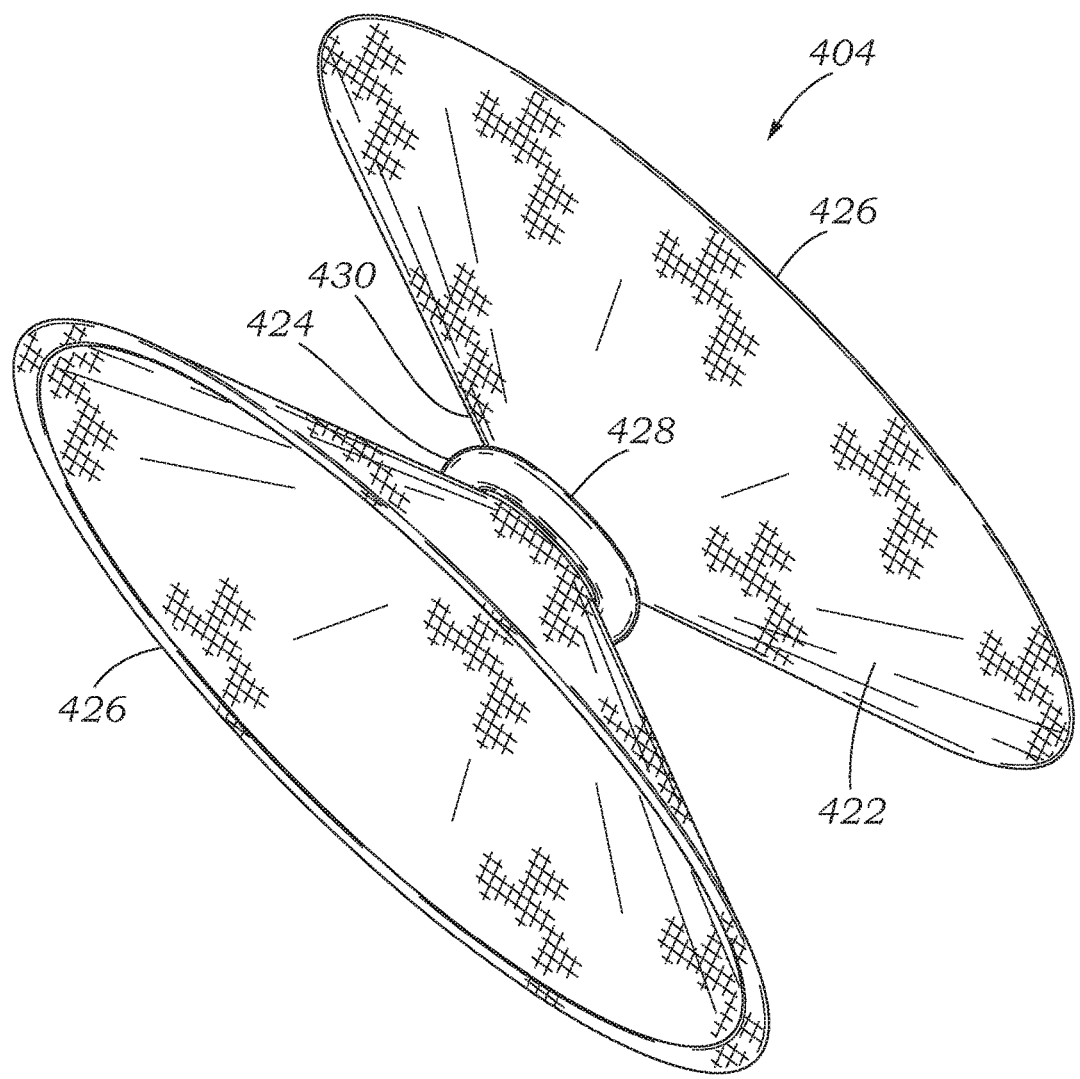
FIG. 21 is a side perspective view of the valve member of the septal closure and port device of FIG. 19 shown apart from the frame.

As best shown in FIG. 21, the valve 404 can comprise a tubular member 422 and an expandable band member 424 that can be centrally disposed around a central portion 430 of the tubular member 422 to form an expandable hole 428 (FIG. 19). The tubular member 422 can include opposing edge portions 426 that can be attached to the frame 402 by means known to those skilled in the art with the benefit of this disclosure, for example by suturing, welding, and/or adhesive bonding.

The tubular member 422 may comprise a suitable biocompatible material, such as any of those materials discussed above for forming flaps 42a, 42b, 42c of the port device 20 or encapsulating layer 314 of the port device 300. For example, the tubular member 422 may comprise a woven (e.g. fabric) material, such as PET fabric. Additionally and/or alternatively, the tubular member 422 may comprise natural tissue or synthetic materials, such as any of various non-woven materials made from any of various polymeric materials. The tubular member 422 can include a low coefficient of friction to allow for smooth passage of catheters or other instruments, for example, the tubular member can comprise a tubular sheet of PTFE or UHMWPE. Additionally and/or alternatively, the tubular member 422 can enable tissue ingrowth on its surface. The band member 424 can comprise any of various suitable biocompatible elastomers, such as PTFE, polyethylene, silicone, or polyurethane.

In some embodiments, the tubular member 422 can comprise an outer fabric layer and an inner polymeric layer formed from a material having a relatively lower coefficient of friction, such as PTFE or UHMWPE.

The band member 424 can have an expanded diameter and an unexpanded diameter. The band member 424 can comprise a biocompatible elastomeric material and can have sufficient elongation properties to seal the valve 404 yet also allow for passage of catheters or other instruments. For example, the elongation properties of the band member 424 can be greater than 300%. When a catheter or other instrument is advanced through the hole 428, the band member 424 can expand such that the hole 428 can expand to allow the instruments crossing. The tubular member 422 can enable smooth advancement of the catheter or other instrument, for example via a low friction material. When the catheter or other instrument is retracted, the band member 424 can relax and reseal the central hole 428.

The band member 424 surrounds and contracts the central portion 430 of the tubular member 422. The excessive material of the central portion 430 gathered by the band member 424 collects to seal the central hole 428. The "free" diameter of the tubular member 422 (i.e. the diameter of the tubular member without the band member) can be approximately the same as the diameter of the central portion 410 of the frame 402.

In some embodiments, the band member 424 can seal the central portion 430 against the outer surface of the medical instrument (e.g., catheter 200) inserted through the port device 400 to prevent or minimize blood flow through the opening 428 when the medical instrument is inserted through the opening. In the illustrated embodiment, the band member 424 is configured such that the opening 428 does not completely close when the medical instrument is removed from the port device and may allow a small amount of blood flow between the left atrium and right atrium through the opening 428. In alternative embodiments, the band member 424 is configured to completely close the opening 428 when the medical instrument is removed from the port device and prevent blood from flowing between the left atrium and right atrium through the opening 428.

In view of the many possible embodiments to which the principles of the disclosed technology may be applied, it should be recognized that the illustrated embodiments are only preferred examples of the disclosure and should not be taken as limiting the scope of the disclosure. Rather, the scope of the disclosure is defined by the following claims. We therefore claim as our disclosure all that comes within the scope and spirit of these claims.

We claim:

1. A method, comprising:
   inserting a delivery catheter into the vasculature of a patient, the delivery catheter comprising a sheath containing a septal closure and port device in a compressed configuration;
   advancing at least a distal end portion of the sheath across an atrial septum of the patient's heart; and
   deploying the closure and port device from the sheath such that a central portion of the closure and port device extends through an orifice in the atrial septum and first and second opposing end portions of the closure and port device are deployed on opposite sides of the septum, which is compressed between the first and second end portions, wherein the closure and port device further comprises a valve member that blocks at least the flow of blood from the left to the right atrium through the central portion.

2. The method of claim 1, further comprising inserting a medical instrument through the valve member and performing a medical procedure in the left side of the heart using the medical instrument.

3. The method of claim 2, wherein the medical instrument comprises a delivery catheter and a prosthetic heart valve carried on a distal end portion of the delivery catheter, and performing the medical procedure comprises implanting the prosthetic heart valve in the native mitral valve annulus of the heart.

4. The method of claim 2, wherein the valve member forms a seal around the outer surface of the medical instrument.

5. The method of claim 2, wherein inserting the medical instrument through the valve member causes the central portion of the closure and port device to expand radially.

6. The method of claim 1, wherein the valve member blocks the flow of blood between the left atrium and right atrium in both directions.

7. The method of claim 1, further comprising creating the orifice in the septum by puncturing the septum prior to deploying the closure and port device.

8. The method of claim 1, wherein the closure and port device comprises an expandable frame defining the central portion and the first and second opposing end portions, and wherein the valve member is supported on the frame and is configured to permit a medical instrument inserted in the right atrium to pass through a lumen in the central portion and the valve member and into the left atrium.

9. The method of claim 8, wherein the frame comprises a plurality of metal frame members.

10. The method of claim 9, wherein each of the first and second end portions comprises a plurality of circumferentially spaced fingers formed by the metal frame members.

11. The method of claim 9, wherein the frame members are encapsulated in a polymeric material.

12. The method of claim 1, wherein the first and second end portions comprise annular flanges that extend substantially perpendicular to the central portion.

13. The method of claim 12, further comprising fabric strips covering outer peripheral edge portions of the flanges to induce tissue in-growth with the covered portions of the flanges.

14. The method of claim 13, wherein each flange comprises an inner surface area bounded by a respective fabric strip, the inner surface area formed from a polymeric material that induces relatively less tissue in-growth than the fabric strip.

15. The method of claim 1, wherein the valve member is secured to the first end portion and extends across a lumen of the central portion.

16. The method of claim 1, wherein the valve member comprise a plurality of flaps, each comprising an angular segment having an outer circumferential edge portion and two radially extending edge portions, the circumferential edge portion secured to the first end portion and each radially extending edge portion placed in an overlapping relationship with an adjacent radially extending edge portion of an adjacent flap, wherein a medical instrument can be inserted through the flaps to access the left atrium.

17. The method of claim 1, wherein the valve member comprises a plurality of circular valve elements layered against each other, each valve element having an aperture or one or more slits to permit passage of a medical instrument through the valve elements.

18. The method of claim 1, wherein the valve member is configured to block the flow of blood between the left atrium and right atrium in both directions when a medical instrument is not inserted through the valve member.

19. A method, comprising:
    inserting a delivery catheter into the vasculature of a patient, the delivery catheter comprising a sheath containing a septal closure and port device in a compressed configuration;
    advancing at least a distal end portion of the sheath across an atrial septum of the patient's heart;
    deploying the closure and port device from the sheath such that a central portion of the closure and port device extends through an orifice in the atrial septum and first and second opposing end portions of the closure and port device are deployed on opposite sides of the septum, which is compressed between the first and second end portions, and wherein the closure and port device is configured to block at least the flow of blood from the left to the right atrium;
    removing the delivery catheter from the vasculature of the patient; and
    after removing the delivery catheter from the patient, inserting a medical instrument through the closure and port device and performing a medical procedure in the left side of the heart using the medical instrument.

20. The method of claim 19, wherein the closure and port device further comprises a valve member, wherein the valve member comprise a plurality of flaps, each comprising an angular segment having an outer circumferential edge portion and two radially extending edge portions, the circumferential edge portion secured to the first end portion and each radially extending edge portion placed in an overlapping relationship with an adjacent radially extending edge portion of an adjacent flap, wherein the medical instrument can be inserted through the flaps to access the left atrium.

\* \* \* \* \*